(12) United States Patent
Oosake

(10) Patent No.: US 10,799,098 B2
(45) Date of Patent: Oct. 13, 2020

(54) MEDICAL IMAGE PROCESSING DEVICE, ENDOSCOPE SYSTEM, DIAGNOSIS SUPPORT DEVICE, AND MEDICAL SERVICE SUPPORT DEVICE

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/677,594

(22) Filed: Nov. 7, 2019

(65) Prior Publication Data

US 2020/0069160 A1 Mar. 5, 2020

Related U.S. Application Data

(63) Continuation of application No. PCT/JP2018/015361, filed on Apr. 12, 2018.

(30) Foreign Application Priority Data

Jun. 2, 2017 (JP) ................. 2017-109923

(51) Int. Cl.
*A61B 1/04* (2006.01)
*A61B 1/00* (2006.01)
(Continued)

(52) U.S. Cl.
CPC ............ *A61B 1/04* (2013.01); *A61B 1/00045* (2013.01); *A61B 1/06* (2013.01); *G06F 9/542* (2013.01);
(Continued)

(58) Field of Classification Search
CPC ....... A61B 1/00045; A61B 1/06; G06F 9/542; G06T 7/0012
See application file for complete search history.

(56) References Cited

U.S. PATENT DOCUMENTS 8,514,086 B2 * 8/2013 Harper ................. A61B 5/7275
340/573.1
2009/0253984 A1 * 10/2009 Yui .................... G01R 33/5635
600/420
(Continued)

FOREIGN PATENT DOCUMENTS

EP 2517614 10/2012
EP 2912991 9/2015
(Continued)

OTHER PUBLICATIONS

"Search Report of Europe Counterpart Application", dated Feb. 4, 2020, p. 1-p. 8.
(Continued)

*Primary Examiner* — Edward Park
(74) *Attorney, Agent, or Firm* — JCIPRNET

(57) ABSTRACT

There are provided a medical image processing device, an endoscope system, a diagnosis support device, and a medical service support device that can allow the observation of a medical image performed by a user not to be obstructed, allow a user not to miss a region of interest, and allow attention required during observation to be continued. An image acquisition unit acquires a medical image including a subject. A medical image is displayed in a first display region (A1) of a monitor. A bounding box, which is notification information, is superimposed and displayed on the medical image in the first display region (A1). In a case where the area of a region of interest is increased, or the like, the notification information is not displayed in the first display region (A1) and an icon, which is separate notification information, is displayed in a second display region (A2) of the monitor.

12 Claims, 9 Drawing Sheets

(51) Int. Cl.
*A61B 1/06* (2006.01)
*G06F 9/54* (2006.01)
*G06T 7/00* (2017.01)

(52) U.S. Cl.
CPC .. *G06T 7/0012* (2013.01); *G06T 2207/10068* (2013.01)

(56) References Cited

U.S. PATENT DOCUMENTS

| | | |
|---|---|---|
| 2011/0021873 A1 | 1/2011 | Ogawa |
| 2012/0130248 A1* | 5/2012 | Fatemi ............... A61B 8/06 600/454 |
| 2014/0049624 A1 | 2/2014 | Masaki et al. |
| 2015/0238126 A1 | 8/2015 | Saito |
| 2018/0249900 A1 | 9/2018 | Imaizumi et al. |

FOREIGN PATENT DOCUMENTS

| | | |
|---|---|---|
| JP | H0727481 | 3/1995 |
| JP | 2006043196 | 2/2006 |
| JP | 2007243275 | 9/2007 |
| JP | 2011027911 | 2/2011 |
| JP | 2011096084 | 5/2011 |
| JP | 2015177961 | 10/2015 |
| WO | 2013146014 | 10/2013 |
| WO | 2017073337 | 5/2017 |
| WO | 2017081976 | 5/2017 |

OTHER PUBLICATIONS

"International Search Report (Form PCT/ISA/210) of PCT/JP2018/015361", dated Jul. 10, 2018, with English translation thereof, pp. 1-5.

"Written Opinion of the International Searching Authority (Form PCT/ISA/237) of PCT/JP2018/015361", dated Jul. 10, 2018, with English translation thereof, pp. 1-14.

"Office Action of Europe Counterpart Application", dated May 18, 2020, p. 1-p. 8.

"Summons to attend oral proceedings pursuant to Rule 115(1) EPC of European Counterpart Application", dated Jul. 9, 2020, p. 1-p. 9.

* cited by examiner

MEDICAL IMAGE PROCESSING DEVICE, ENDOSCOPE SYSTEM, DIAGNOSIS SUPPORT DEVICE, AND MEDICAL SERVICE SUPPORT DEVICE

CROSS-REFERENCE TO RELATED APPLICATIONS

This application is a Continuation of PCT International Application No. PCT/JP2018/015361 filed on Apr. 12, 2018, which claims priority under 35 U.S.C § 119(a) to Japanese Patent Application No. 2017-109923 filed on Jun. 2, 2017. Each of the above application(s) is hereby expressly incorporated by reference, in its entirety, into the present application.

BACKGROUND OF THE INVENTION

1. Field of the Invention

The present invention relates to a medical image processing device, an endoscope system, a diagnosis support device, and a medical service support device providing notification information, which is to be notified to a user, by using a medical image.

2. Description of the Related Art

A medical image processing device, which uses a medical image as with an endoscope system comprising a light source device, an endoscope, and a processor device, is being spread in the current medical field. Further, in recent years, a region of interest, which is an object to be diagnosed, has been detected from the analysis of a medical image and has been notified to a user. In addition, the error of a subject or a medical image, the observation state of a subject, whether or not a lesion is present, the type of a lesion, and the like also have been notified.

In a case where the above-mentioned notification information to be notified to a user is to be displayed and provided on the monitor, the observation of a medical image performed by a user is required not to be obstructed as much as possible. For this purpose, a method of preventing a region of a medical image, which is to be noticed, and notification information from overlapping each other as disclosed in JP2011-096084A is considered by reference to, for example, a technique for preventing an operation cursor, which is displayed on a main screen, from overlapping a sub-screen. Further, a method of making notification information not be displayed after a lapse of a fixed time as disclosed in JP2007-243275A is considered by reference to a technique for making necessary information, such as a clock, not be displayed after a lapse of a fixed time. Furthermore, a method of stopping displaying a medical image and displaying only notification information at the time of generation of an error as disclosed in JP1995-027481B (JP-H-07-027481B) is considered by reference to a technique for switching a normal image to an abnormality message at the time of detection of abnormality.

SUMMARY OF THE INVENTION

In a case where notification information is to be provided to a user, not only the observation of a medical image performed by a user is required not to be obstructed as much as possible as described above but also the missing of a region of interest needs to be prevented and attention required during observation needs to be continued. Accordingly, in a case where notification information is made not to be displayed as disclosed in JP2007-243275A, there is a concern that a region of interest may be missed. Further, even in a case where the display of a medical image is stopped as disclosed in JP1995-027481B (JP-H-07-027481B), there is a concern that a region of interest may be missed. With regard to JP2011-096084A, since a region where the operation cursor is positioned may not necessarily be a region of interest, the sub-screen displaying notification information and the region of interest may overlap each other.

An object of the invention is to provide a medical image processing device, an endoscope system, a diagnosis support device, and a medical service support device that can allow the observation of a medical image performed by a user not to be obstructed, allow a user not to miss a region of interest, and allow attention required during observation to be continued.

A medical image processing device of the invention comprises an image acquisition unit that acquires a medical image including a subject; a display unit that displays the medical image in a first display region; and a display control unit that performs control to make notification information, which is to be notified to a user, be displayed on the display unit or control to make the notification information not be displayed on the display unit.

It is preferable that the display control unit performs control to make the notification information be displayed in a second display region different from the first display region or control to make the notification information, which is being displayed, not be displayed in the second display region. It is preferable that the display control unit performs control to make the notification information be displayed in the first display region in a case where a first condition is satisfied, and the display control unit performs control to make the notification information, which is being displayed in the first display region, not be displayed and to make the notification information be displayed in the second display region different from the first display region in a case where a second condition different from the first condition is satisfied.

It is preferable that the medical image processing device further comprises a region-of-interest detection section that detects a region of interest from the medical image, the first condition is a case where an area of the region of interest is equal to or smaller than a threshold value for an area, and the second condition is a case where the area of the region of interest exceeds the threshold value for an area. It is preferable that the medical image processing device further comprises a region-of-interest detection section that detects a region of interest from the medical image, the first condition is a case where a position of the region of interest is away from a central range of the first display region, and the second condition is a case where the position of the region of interest is in the central range of the first display region.

It is preferable that the medical image processing device further comprises a region-of-interest detection section that detects a region of interest from the medical image, the first condition is a case where a temporal variation of the region of interest exceeds a threshold value for variation, and the second condition is a case where the temporal variation of the region of interest is equal to or smaller than the threshold value for variation. It is preferable that the medical image processing device further comprises a region-of-interest detection section that detects a region of interest from the medical image, the first condition is a case where a luminance value of the region of interest is equal to or smaller than a threshold value for a luminance value, and the second condition is a case where the luminance value of the region of interest exceeds the threshold value for a luminance value.

It is preferable that the first condition is a case where a first display time in which the notification information is displayed in the first display region is equal to or shorter than a display limit time, and the second condition is a case where the first display time exceeds the display limit time. It is preferable that the first condition is a case where a region where the notification information is to be displayed is designated as the first display region by a user's input, and the second condition is a case where the region where the notification information is to be displayed is designated as the second display region by a user's input.

It is preferable that the medical image processing device further comprises a region-of-interest detection section that detects a region of interest from the medical image; the first condition is a case where combination information in which at least two of an area of the region of interest, a position of the region of interest, a temporal variation of the region of interest, a luminance value of the region of interest, or a first display time in which the notification information is displayed in the first display region are combined satisfies a condition for combination; and the second condition is a case where the combination information does not satisfy the condition for combination. It is preferable that the first condition is a case where area-luminance combination information in which the area of the region of interest and the luminance value of the region of interest are combined satisfies a combination condition for area-luminance, and the second condition is a case where the area-luminance combination information does not satisfy the combination condition for area-luminance.

It is preferable that the display control unit performs control to make the notification information, which is being displayed, not be displayed in the second display region in a case where a third condition different from the first condition and the second condition is satisfied.

It is preferable that the display control unit performs control to make the notification information be displayed or control to make the notification information not be displayed in any one of the first display region, the second display region different from the first display region, or both the first display region and the second display region in a case where a specific condition is satisfied, and the display control unit performs control to make the notification information be displayed or control to make the notification information not be displayed in a display region, which is different from the display region used in the case where the specific condition is satisfied, in a case where the specific condition is not satisfied.

It is preferable that the display control unit performs control to superimpose and display the notification information on the medical image in the first display region.

It is preferable that the medical image processing device further comprises a region-of-interest detection section that detects a region of interest from the medical image, and the notification information is notification information used for notification of information about the region of interest.

It is preferable that the medical image processing device further comprises an error detection section that detects an error of the subject or the medical image, and the notification information is the error. It is preferable that the error detection section is an image analysis section for error detection analyzing the medical image to detect the error. It is preferable that the error is a blur appearing on the medical image. It is preferable that the error is a degree of contamination of the subject. It is preferable that the error detection section is a sensor for error detection.

It is preferable that the notification information is an observation state of the subject. It is preferable that the observation state is represented as at least one of an illumination mode that is related to illumination light with which the subject is to be irradiated, an image processing mode that is related to image processing to be performed on the medical image, enlargement observation where the subject is enlarged, or non-enlargement observation where the subject is not enlarged. It is preferable that the notification information is whether or not a lesion is present, the type of a lesion, or a detection state of a treatment tool.

It is preferable that the notification information is superimposed on the medical image and is stored. It is preferable that the notification information and the medical image are stored together as one data format. It is preferable that the notification information and the medical image are stored as at least two separate data.

According to the invention, it is possible to allow the observation of a medical image performed by a user not to be obstructed, to allow a user not to miss a region of interest, and to allow attention required during observation to be continued.

Figure 6:
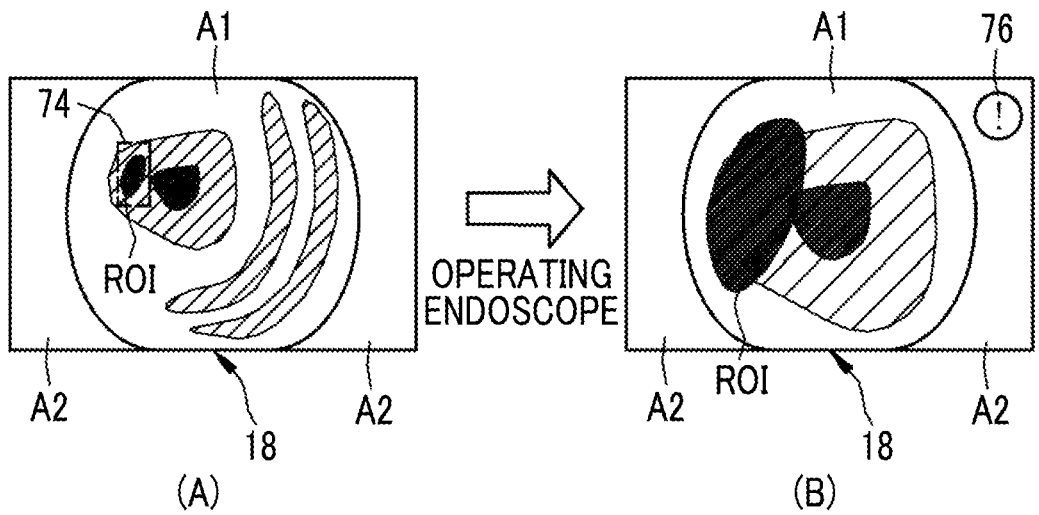

(A) of FIG. 6 is an image diagram in which a bounding box is displayed as notification information in a case the area of a region of interest is small, and (B) of FIG. 6 is an image diagram in which an icon is displayed as notification information in a case where the area of the region of interest is large.

Figure 7:
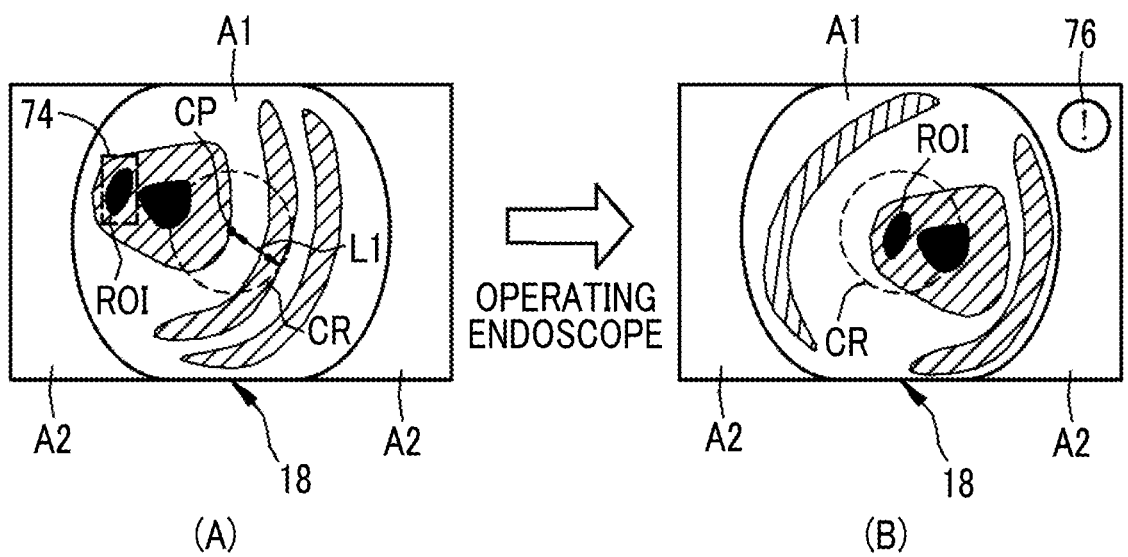

(A) of FIG. 7 is an image diagram in which a bounding box is displayed as notification information in a case where a region of interest is away from a central range, and (B) of FIG. 7 is an image diagram in which an icon is displayed as notification information in a case where the region of interest is in the central range.

Figure 8:
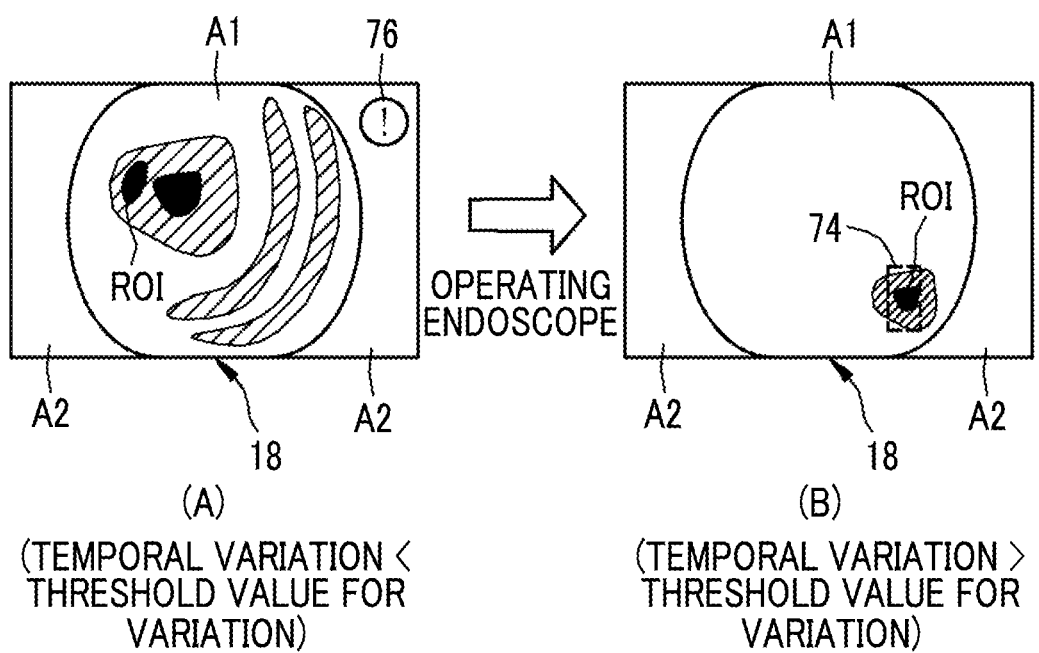

(A) of FIG. 8 is an image diagram in which an icon is displayed as notification information in a case where the movement of a region of interest is slow, and (B) of FIG. 8 is an image diagram in which a bounding box is displayed as notification information in a case where the movement of the region of interest is fast.

Figure 9:
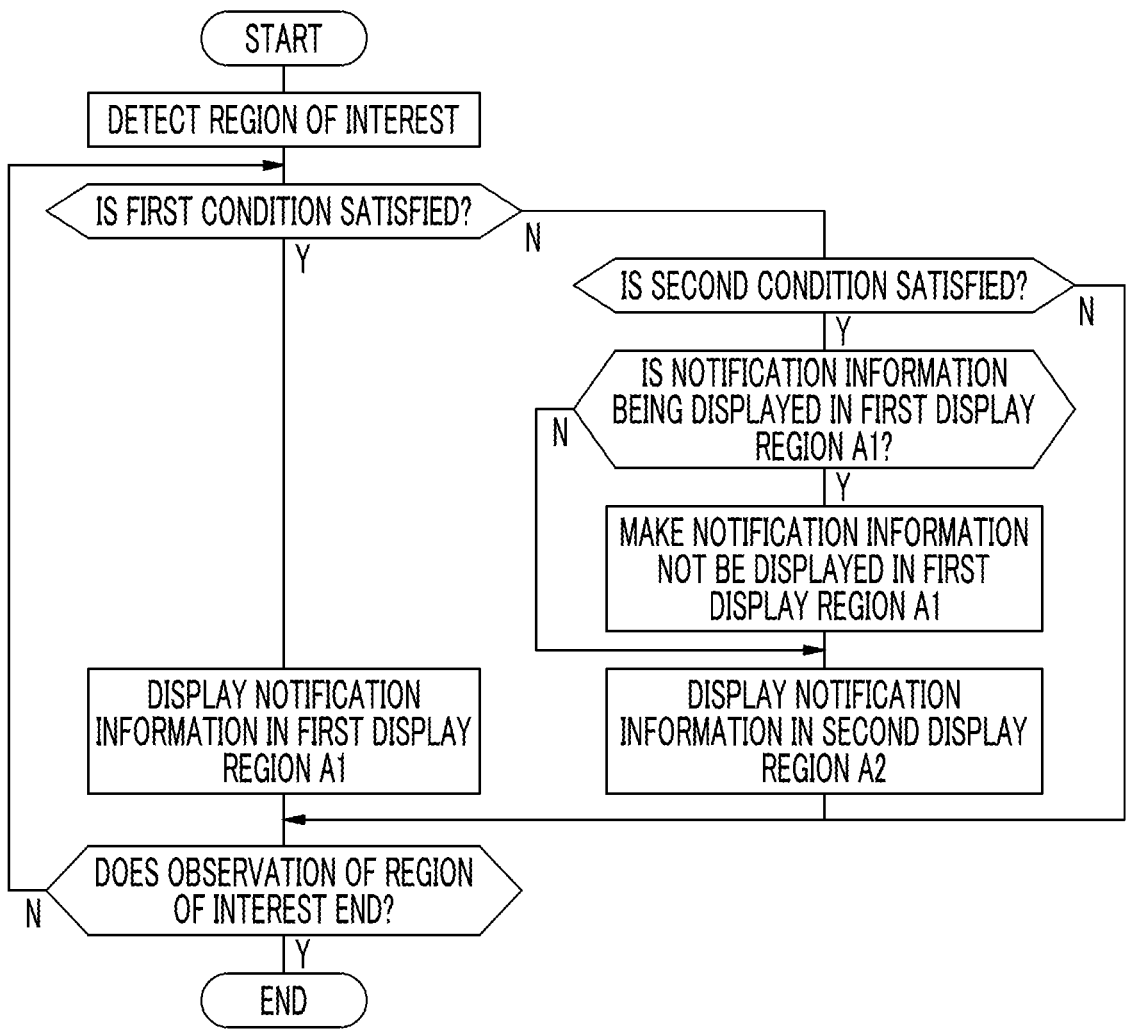

FIG. 9 is a flowchart showing a series of flows of the control of display of notification information.

Figure 10:
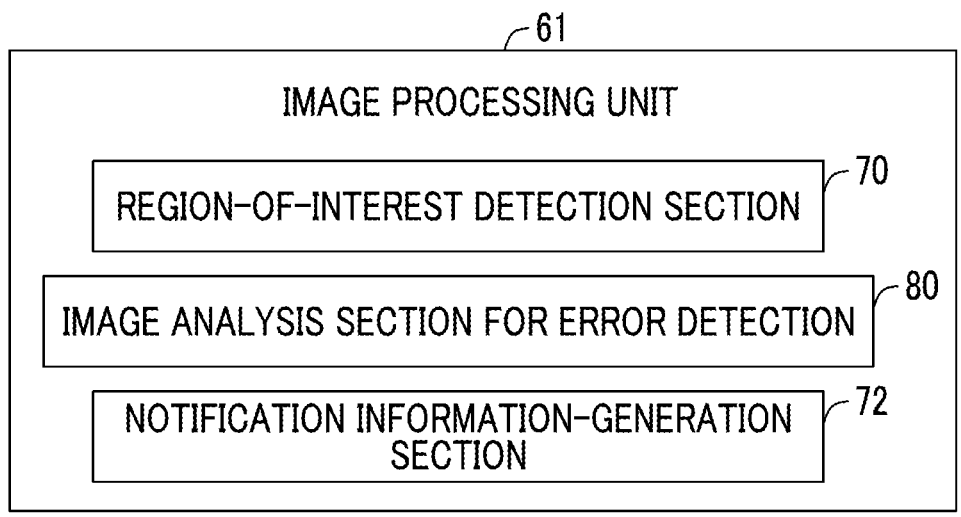

FIG. 10 is a block diagram of an image processing unit of a second embodiment.

Figure 11:
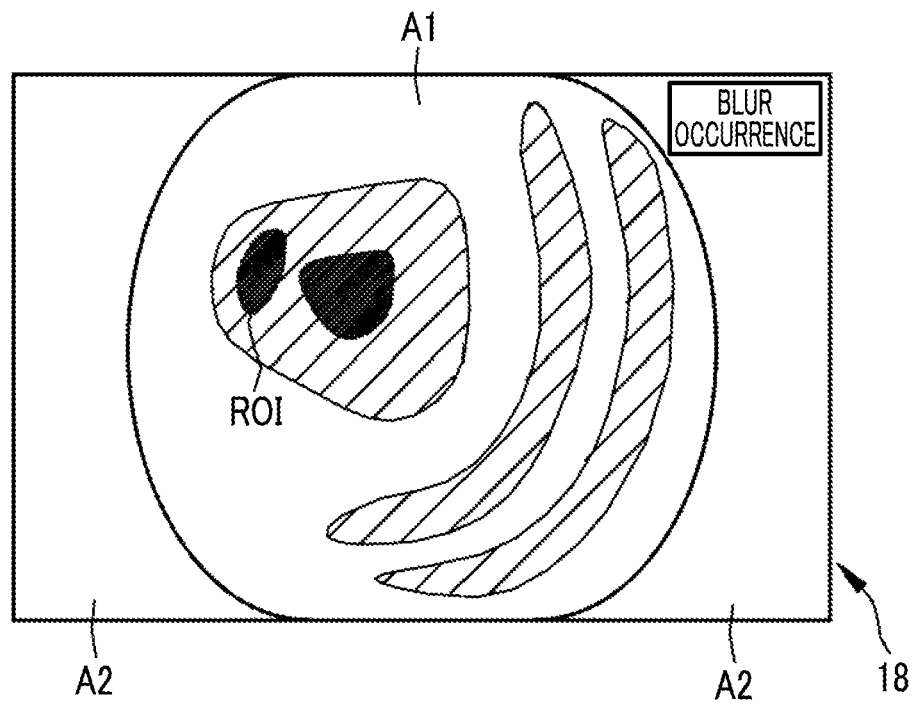

FIG. 11 is an image diagram in which character information of "blur occurrence" is displayed as notification information.

Figure 12:
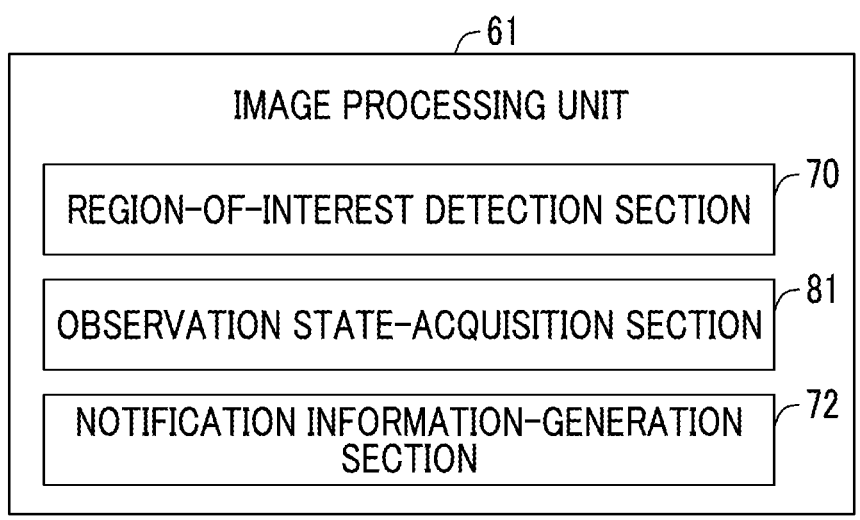

FIG. 12 is a block diagram of an image processing unit of a third embodiment.

Figure 13:
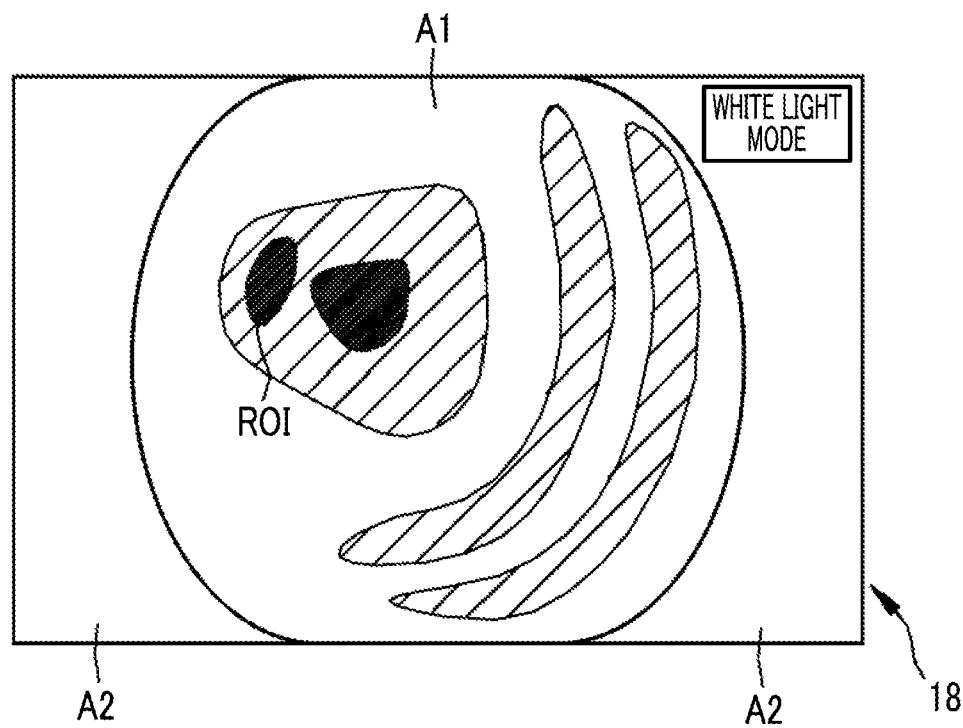

FIG. 13 is an image diagram in which character information of "white light mode" is displayed as notification information.

Figure 14:
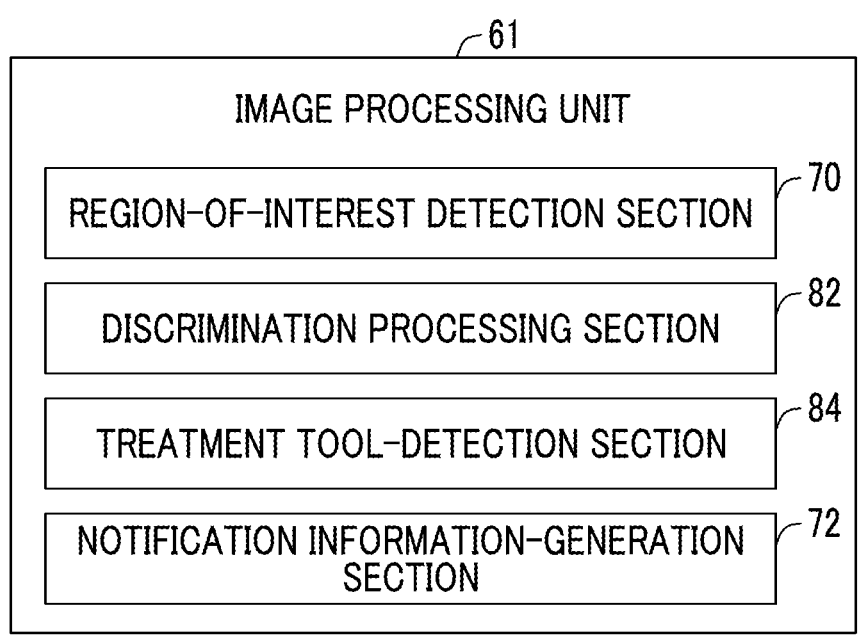

FIG. 14 is a block diagram of an image processing unit of a fourth embodiment.

Figure 15:
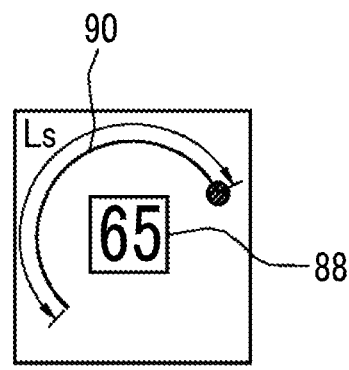

FIG. 15 is a diagram showing a discrimination score value and a seek bar.

Figure 16:
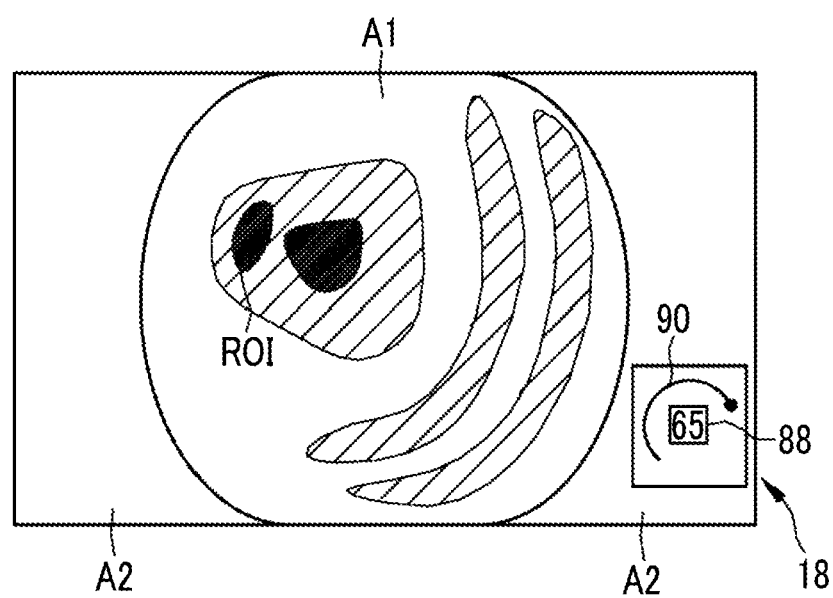

FIG. 16 is an image diagram in which a discrimination score value and a seek bar are displayed as notification information.

DESCRIPTION OF THE PREFERRED EMBODIMENTS

First Embodiment

Figure 1:
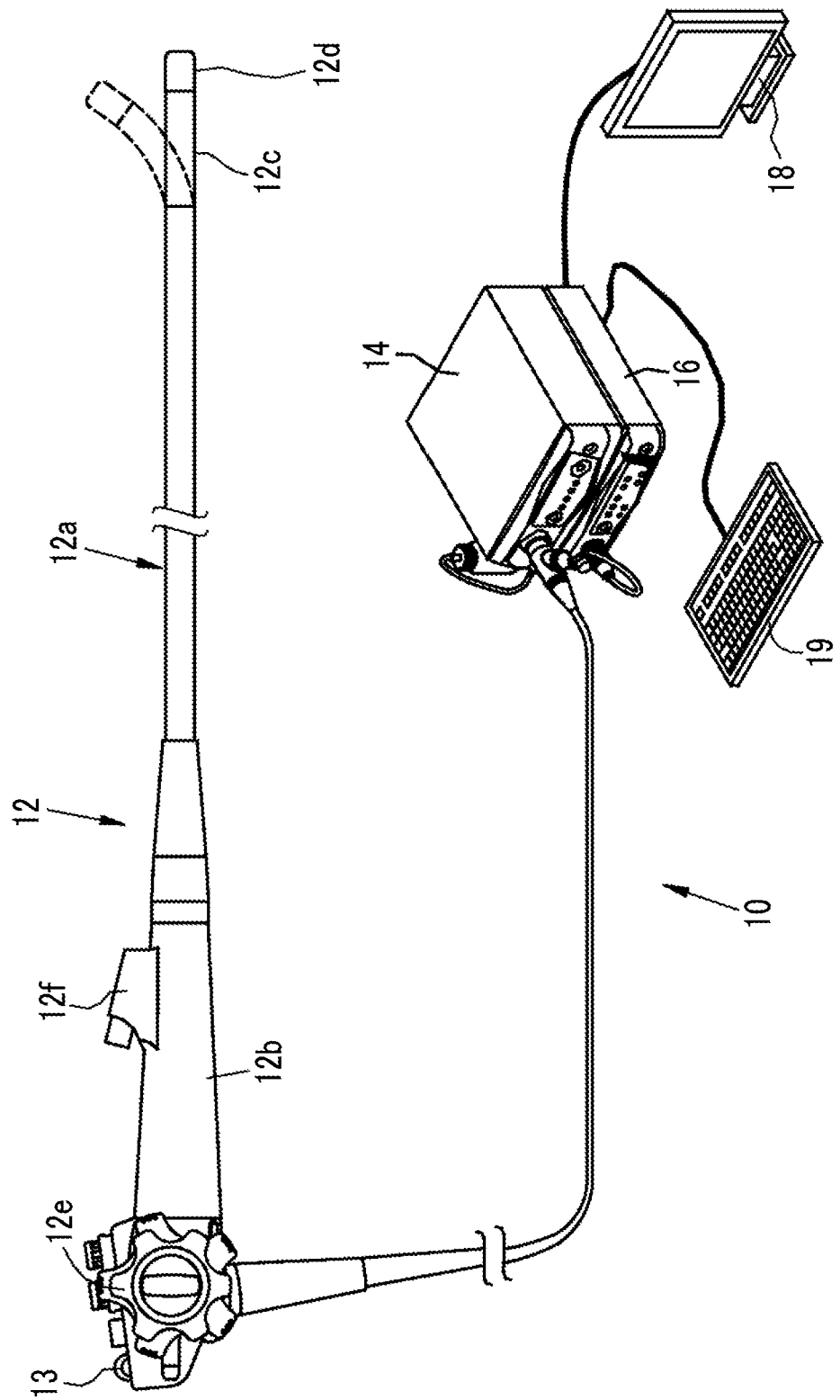
FIG. 1 is a diagram showing the appearance of an endoscope system.

As shown in FIG. 1, an endoscope system 10 comprises an endoscope 12, a light source device 14, a processor device 16, a monitor 18, and a console 19. The endoscope 12 irradiates a subject, which is an object to be observed, with illumination light and picks up the image of the subject that is irradiated with the illumination light. The light source device 14 generates illumination light with which the subject is to be irradiated. The processor device 16 performs the control of the endoscope system 10, image processing, and the like. The monitor 18 is a display unit that displays an image output from the processor device 16. The console 19 is an input device, which is used to perform setting input for the processor device 16 or the like, such as a keyboard.

The endoscope 12 includes an insertion part 12a that is to be inserted into an object to be examined, an operation part 12b that is provided at the proximal end portion of the insertion part 12a, a bendable part 12c that is provided on the distal end side of the insertion part 12a, and a distal end part 12d. The bendable part 12c is bent by the operation of an angle knob 12e of the operation part 12b. Since the bendable part 12c is bent, the distal end part 12d faces in a desired direction. The distal end part 12d is provided with a jet port (not shown) that jets air, water, or the like toward a subject.

Further, the operation part 12b is provided with a zoom operation part 13 in addition to the angle knob 12e. The image of a subject can be picked while being enlarged or reduced in size by the operation of the zoom operation part 13. Furthermore, a forceps channel (not shown) into which a treatment tool or the like is to be inserted is provided over the distal end part 12d from the insertion part 12a. The treatment tool is inserted into the forceps channel through a forceps inlet 12f.

Figure 2:
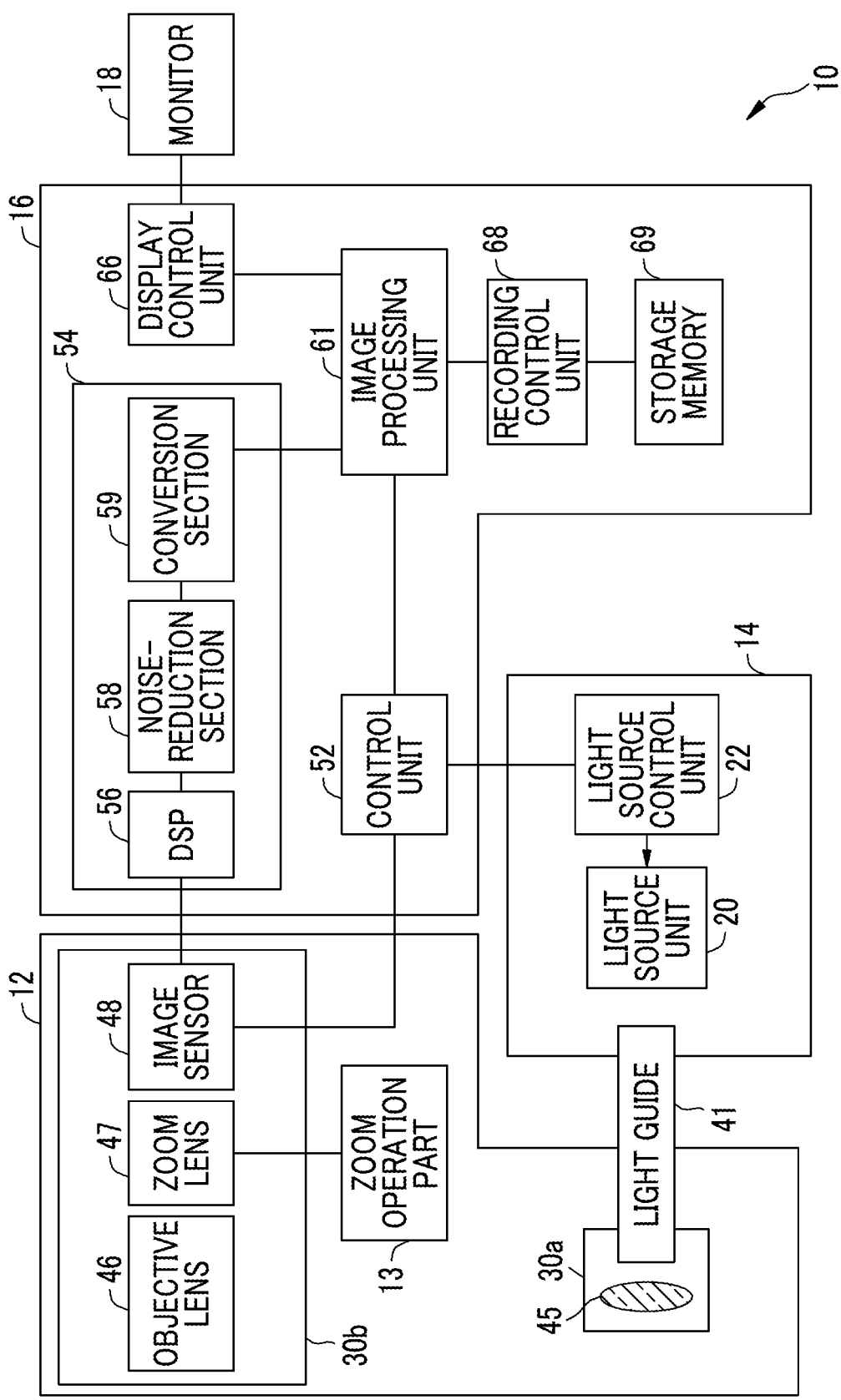
FIG. 2 is a block diagram of the endoscope system.

As shown in FIG. 2, the light source device 14 comprises a light source unit 20 and a light source control unit 22. The light source unit 20 emits illumination light for illuminating a subject. The light source unit 20 comprises one or a plurality of light sources. The light source control unit 22 controls the drive of the light source unit 20. The light source control unit 22 independently controls the timing of the turn-on or turn-off of the light source of the light source unit 20, the amount of light to be emitted at the time of turn-on, and the like. As a result, the light source unit 20 can emit a plurality of kinds of illumination light of which the amounts of light to be emitted or light emission timings are different from each other.

The illumination light emitted from the light source unit 20 is incident on a light guide 41. The light guide 41 is built in the endoscope 12 and a universal cord, and transmits the illumination light to the distal end part 12d of the endoscope 12. The universal cord is a cord that connects the endoscope 12 to the light source device 14 and the processor device 16.

A multimode fiber can be used as the light guide 41. For example, a thin fiber cable of which a total diameter of a core diameter of 105 μm, a cladding diameter of 125 μm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and illumination light is emitted to a subject through the illumination lens 45. The image pickup optical system 30b includes an objective lens 46, a zoom lens 47, and an image sensor 48. The image sensor 48 picks up the image of the subject by using the reflected light of the illumination light, which returns from the subject through the objective lens 46 and the zoom lens 47, and the like (including scattered light, fluorescence emitted from the subject, fluorescence caused by a medicine administered to the subject, and the like in addition to the reflected light). The zoom lens 47 is moved by the operation of the zoom operation part 13, and enlarges or reduces the image of the subject to be picked up by the image sensor 48.

The image sensor 48 is a color sensor including, for example, primary color filters, and comprises three kinds of pixels of B pixels (blue pixels) including blue color filters, G pixels (green pixels) including green color filters, and R pixels (red pixels) including red color filters. The blue color filter mainly transmits violet to blue light. The green color filter mainly transmits green light. The red color filter mainly transmits red light. In a case where the image of a subject is picked up using the primary color image sensor 48 as described above, a maximum of three kinds of images of a B image (blue image) obtained from the B pixels, a G image (green image) obtained from the G pixels, and an R image (red image) obtained from the R pixels can be obtained at the same time.

A charge coupled device (CCD) sensor or a complementary metal oxide semiconductor (CMOS) sensor can be used as the image sensor 48. Further, the image sensor 48 of this embodiment is a primary color sensor, but a complementary color sensor can also be used. A complementary color sensor includes, for example, cyan pixels including cyan color filters, magenta pixels including magenta color filters, yellow pixels including yellow color filters, and green pixels including green color filters. In a case where a complementary color sensor is used, images obtained from the respective color pixels can be converted into a B image, a G image, and an R image through complementary color-primary color conversion. Further, a monochrome sensor, which includes no color filter, can be used as the image sensor 48 instead of a color sensor. In this case, the images of a subject are sequentially picked up using illumination lights having the respective colors, such as B, G, and R, so that images having the respective colors can be obtained.

The processor device 16 includes a control unit 52, an image acquisition unit 54, an image processing unit 61, a display control unit 66, a recording control unit 68, and a storage memory 69. The control unit 52 performs the general control of the endoscope system 10, such as the synchronization control of the irradiation timing of illumination light and an image pickup timing. Further, in a case where various kinds of settings are input using the console 19 or the like, the control unit 52 inputs the setting to each part of the endoscope system 10, such as the light source control unit 22, the image sensor 48, or the image processing unit 61.

The image acquisition unit 54 acquires the picked-up image of the subject from the image sensor 48. Since the image acquired by the image acquisition unit 54 is an image obtained by a medical device, such as the endoscope 12, the image acquired by the image acquisition unit 54 is referred to as a medical image. The image acquisition unit 54 includes a digital signal processor (DSP) 56, a noise-reduction section 58, and a conversion section 59, and performs various kinds of processing on the acquired medical image as necessary. The DSP 56 performs various kinds of processing, such as defect correction processing, offset processing, gain correction processing, linear matrix processing, gamma conversion processing, demosaicing, and YC conversion processing, on the acquired medical image as necessary.

The defect correction processing is processing for correcting the pixel value of a pixel corresponding to a defective pixel of the image sensor 48. The offset processing is processing for reducing a dark current component from the image having been subjected to the defect correction processing and setting an accurate zero level. The gain correction processing is processing for adjusting the signal level of each image by multiplying the image, which has been subjected to the offset processing, by a gain. The linear matrix processing is processing for improving the color reproducibility of the image subjected to the offset processing, and the gamma conversion processing is processing for adjusting the brightness or chroma of the image having been subjected to the linear matrix processing.

The demosaicing is performed in a case where the image sensor 48 is a color sensor. The demosaicing (also referred to as equalization processing or demosaicing processing) is processing for interpolating the pixel value of a missing pixel, and is performed on the image having been subjected to the gamma conversion processing. The missing pixel is a pixel that does not have a pixel value (since pixels having other colors are disposed in the image sensor 48) due to the arrangement of color filters. For example, since a B image is an image that is obtained from the image pickup of a subject at B pixels, pixels of the B image, which are present at positions corresponding to a G pixel and an R pixel, do not have a pixel value. In the demosaicing, the pixel values of pixels of a B image, which are present at positions corresponding to a G pixel and an R pixel of the image sensor 48, are generated through the interpolation of the B image. The YC conversion processing is processing for converting an image, which has been subjected to the demosaicing, into luminance channels Y, color-difference channels Cb, and color-difference channels Cr.

The noise-reduction section 58 performs noise-reduction processing on the luminance channels Y, the color-difference channels Cb, and the color-difference channels Cr by using, for example, a moving-average method, a median filter method, or the like. The conversion section 59 converts the luminance channels Y, the color-difference channels Cb, and the color-difference channels Cr, which have been subjected to the noise-reduction processing, into an image having the respective colors of BGR again.

The image processing unit 61 performs various kinds of image processing on the medical image that is acquired by the image acquisition unit 54. In this embodiment, the image processing unit 61 generates notification information that is to be notified to a user. The image processing unit 61 sends the notification information and the medical image to the display control unit 66 or the recording control unit 68. The details of the image processing unit 61 will be described in detail later.

The display control unit 66 converts the notification information and the medical information, which are sent from the image processing unit 61, into a format suitable to be displayed on the monitor 18, and outputs the converted notification information and the converted medical information to the monitor 18. Accordingly, at least the medical image and the notification information are displayed on the monitor 18. In this embodiment, the display control unit 66 performs control to make the notification information be displayed on the monitor 18 or control to make the notification information not be displayed on the monitor 18. The details of the display control unit 66 will be described later.

The recording control unit 68 converts the notification information and the medical image, which are sent from the image processing unit 61, into a format suitable to be stored in the storage memory 69, and records the converted notification information and the converted medical image in the storage memory 69. There are a case where the recording control unit 68 controls recording according to the control performed by the display control unit 66 and a case where the recording control unit 68 controls recording regardless of the control performed by the display control unit 66. In the case where the recording control unit 68 controls recording according to the control performed by the display control unit 66, for example, at a timing when the notification information is made to be displayed by the display control unit 66, the notification information and the medical image at that point of time are stored in the storage memory 69 by the recording control unit 68. On the other hand, in the case where the recording control unit 68 controls recording regardless of the control performed by the display control unit 66, for example, at a timing when a region of interest is detected by the image processing unit 61, the notification information and the medical image at that point of time are stored in the storage memory 69 by the recording control unit 68.

In a case where the recording control unit 68 stores the notification information and the medical image in the storage memory 69, the recording control unit 68 may superimpose the notification information on the medical image and store the notification information and the medical image in the storage memory 69 or may store the notification information and the medical image in the storage memory 69 as at least two separate data. Further, in a case where the recording control unit 68 stores the notification information and the medical image in the storage memory 69 together as one data, it is preferable that the recording control unit 68 stores the notification information and the medical image as a data format, such as PNG, Exif, GIF, or MP4.

Figure 3:
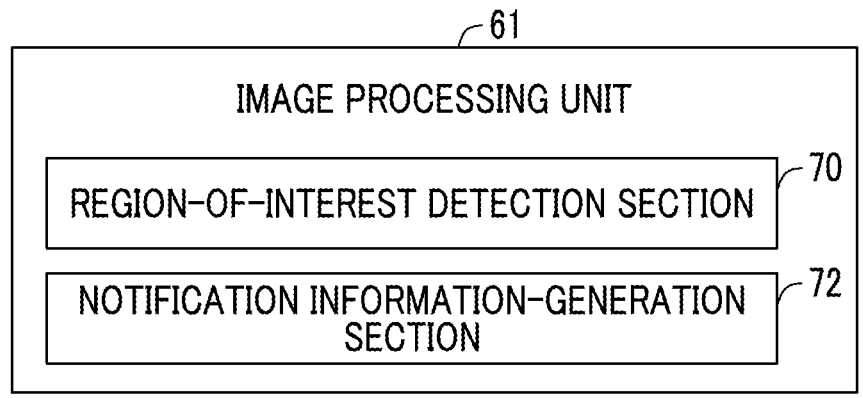
FIG. 3 is a block diagram of an image processing unit of a first embodiment.

As shown in FIG. 3, the image processing unit 61 comprises a region-of-interest detection section 70 and a notification information-generation section 72. The region-of-interest detection section 70 detects a region of interest, which is to be noticed as an object to be examined or diagnosed, from the medical image. For example, the region-of-interest detection section 70 not only performs a convolutional neural network for the medical image but also detects a region of interest on the basis of a feature quantity that is obtained from the color information of the medical image, the gradient of pixel values, and the like. The gradient of pixel values, and the like are changed depending on, for example, the shape (the overall undulation, the local recess, or the protuberance, of a mucous membrane, or the like), the color (a color, such as whitening caused by inflammation, bleeding, redness, or atrophy), the characteristics of a tissue (the thickness, the depth, or the density of a blood vessel, a combination thereof, or the like), the characteristics of structure (a pit pattern, and the like), or the like of a subject.

The region of interest, which is detected by the region-of-interest detection section 70, is a region including, for example, a lesion part typified by a cancer, a benign tumor, an inflamed part (including a part where a change, such as bleeding or atrophy, occurs in addition to so-called inflammation), a cautery mark caused by heating or a marking portion marked by coloration using a colorant, a fluorescent agent, or the like, or a biopsy portion where biopsy is performed. That is, a region including a lesion; a region where a lesion is likely to occur; a region that has been subjected to a certain treatment, such as biopsy; a treatment tool, such as a clip or forceps; a region where detailed observation is needed regardless of the possibility of a lesion, such as a dark region (a region where observation light does not easily reach since the region is positioned on the back of a fold or in a lumen); or the like may be the region of interest. In the endoscope system 10, the region-of-interest detection section 70 detects a region, which includes at least one of the lesion part, the benign tumor, the inflamed part, the marking portion, or the biopsy portion, as the region of interest.

Figure 4:
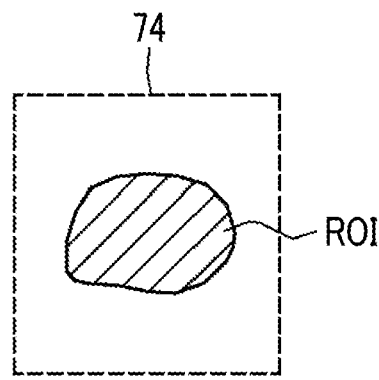
FIG. 4 is a diagram showing a bounding box that is one of notification information.

The notification information-generation section 72 generates notification information, which is used for the notification of information about the region of interest, on the basis of the region of interest that is detected by the region-of-interest detection section 70. Specifically, the notification information-generation section 72 generates a rectangular bounding box 74, which surrounds the region of interest ROI with a dotted line, as the notification information as shown in FIG. 4. Alternatively, the notification information-generation section 72 may generate an arrow that indicates the region of interest, an icon (see an icon 76 of FIG. 6) representing that the region of interest is being detected, or the like as the notification information. Further, color information about a color, which allows the region of interest to be distinguished from other regions, may be used as the notification information. It is preferable that the notification information-generation section 72 generates a plurality of pieces of notification information suitable for the control of display to be capable of displaying different kinds of notification information according to the control of display performed by the display control unit 66.

Figure 5:
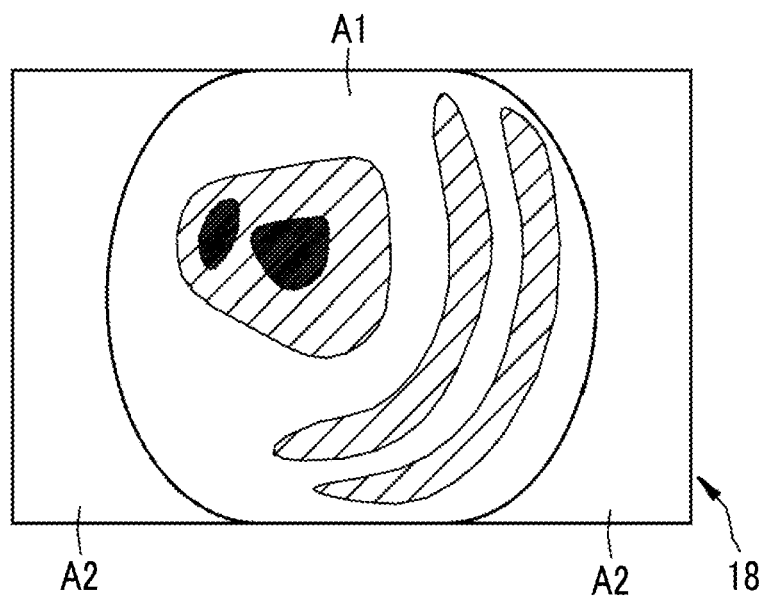
FIG. 5 is an image diagram showing a first display region A1 and a second display region A2 of a monitor.

As shown in FIG. 5, the display control unit 66 performs control to make the medical image be displayed on in a first display region A1 of the monitor 18. Further, the display control unit 66 performs control to make notification information be displayed on the monitor 18 and control to make notification information, which is being displayed, not be displayed on the monitor 18. Specifically, the display control unit 66 performs control to make notification information be displayed in the first display region A1 and to make notification information, which is being displayed, not be displayed in the first display region. Furthermore, the display control unit 66 performs control to make notification information be displayed in a second display region A2 different from the first display region of the monitor 18 and to make notification information, which is being displayed, not be displayed. In a case where notification information is made to be displayed in the first display region A1, it is preferable that the notification information is superimposed and displayed on the medical image.

Further, the display control unit 66 performs control to make notification information be displayed in both the first display region A1 and the second display region A2 and to make notification information, which is being displayed, not be displayed in at least one of the first display region A1 or the second display region A2. In a case where notification information is made to be displayed in the first display region A1, the display control unit 66 performs control to superimpose and display the notification information on the medical image that is being displayed in the first display region A1.

Here, the first display region A1 is a region that includes the image of a subject positioned at least on the front side of the endoscope 12. The second display region A2 is a region that includes the image of a subject positioned substantially at least on the lateral side or the rear side of the endoscope 12. In this embodiment, the first display region A1 is a barrel-shaped region and the second display region A2 is a part of the entire screen of the monitor 18 except for the barrel-shaped first display region A1.

The display control unit 66 controls the display of the notification information so that the display of the notification information does not obstruct the observation of the region of interest. Specifically, the display control unit 66 makes the notification information be displayed in the first display region A1 in a case where a first condition is satisfied, and makes notification information, which is being displayed in the first display region, not be displayed and displays notification information in the second display region A2 in a case where a second condition different from the first condition is satisfied.

For example, the first condition may be a case where the area of the region of interest is equal to or smaller than a threshold value for an area, and the second condition may be a case where the area of the region of interest exceeds the threshold value for an area. In this case, the display control unit 66 performs control to superimpose and display a bounding box 74, which surrounds the region of interest ROI, on the first display region A1 as the notification information as shown in (A) of FIG. 6 in a case where the area of the region of interest ROI is equal to or smaller than the threshold value for an area (in a case where the first condition is satisfied). Since the bounding box 74 is superimposed and displayed in this way, a user can reliably recognize the region of interest even in a case where the region of interest ROI is small.

After that, in a case where the medical image displayed in the first display region A1 is changed by the operation of the endoscope 12, the area of the region of interest is also changed according to a change in the medical image. In this case, the size of the bounding box 74 is also increased according to an increase in the size of the region of interest in a case where the size of the region of interest displayed in the medical image is increased. For this reason, there is a case where the bounding box 74 of which the size is increased in this way obstructs the observation of the medical image. Accordingly, in a case where the area of the region of interest ROI exceeds the threshold value for an area (in a case where the second condition is satisfied), the display control unit 66 makes the bounding box 74 not be displayed in the first display region A1 as shown in (B) of FIG. 6. Further, the display control unit 66 makes the icon 76, which represents that the region of interest ROI is being detected, be displayed in the second display region A2 as the notification information. Accordingly, even though the bounding box 74 is made not to be displayed in the first display region A1, it is possible to prevent the region of interest from being missed.

Furthermore, the first condition may be a case where the position of the region of interest is away from the central range of the first display region A1, and the second condition may be a case where the position of the region of interest is in the central range of the first display region A1. Here, a central range CR of the first display region A1 means a range that is within a previously set distance L1 from a center CP of the first display region (see (A) of FIG. 7). In a case where the position of the region of interest ROI is away from the central range CR (in a case where the first condition is satisfied), it is difficult for a user to recognize the region of interest ROI. For this reason, the bounding box 74 surrounding the region of interest ROI is superimposed and displayed as the notification information as shown in (A) of FIG. 7.

After that, in a case where the medical image displayed in the first display region A1 is changed by the operation of the endoscope 12, the position of the region of interest is also changed according to a change in the medical image. In this case, a user can recognize the region of interest even though the bounding box 74 is not displayed in a case where the region of interest having been away from the central range CR enters the central range CR. Accordingly, in a case where the region of interest ROI is in the central range CR (in a case where the second condition is satisfied), the display control unit 66 makes the bounding box 74 not be displayed in the first display region A1 as shown in (B) of FIG. 7. Further, the display control unit 66 makes the icon 76, which represents that the region of interest ROI is being detected, be displayed in the second display region A2 as the notification information. Accordingly, even though the bounding box 74 is made not to be displayed in the first display region A1, it is possible to prevent the region of interest from being missed.

Furthermore, the first condition may be a case where the temporal variation of the region of interest exceeds a threshold value for variation, and the second condition may be a case where the temporal variation of the region of interest is equal to or smaller than the threshold value for variation. Here, the temporal variation of the region of interest means, for example, the moving distance of the region of interest within a specific time. In a case where the temporal variation of the region of interest ROI is equal to or smaller than the threshold value for variation (in a case where the second condition is satisfied), the display control unit 66 makes the icon 76, which represents that the region of interest ROI is being detected, be displayed in the second display region A2 as the notification information as shown in (A) of FIG. 8. Since a user can grasp the region of interest in a case where the movement of the region of interest is slow as described above, it is preferable that only the icon 76 is displayed to call user's attention.

Further, in a case where the movement of the region of interest becomes fast, or the like, the display control unit 66 makes the bounding box 74, which surrounds the region of interest ROI, be displayed in the first display region A1 as the notification information as shown in (B) of FIG. 8 with a case where the temporal variation of the region of interest ROI exceeds the threshold value for variation (a case where the first condition is satisfied). Accordingly, even though the movement of the region of interest becomes fast, a user can grasp the position of the region of interest and reliably make a diagnosis.

Furthermore, the first condition may be a case where the luminance value of the region of interest is equal to or smaller than a threshold value for a luminance value, and the second condition may be a case where the luminance value of the region of interest exceeds the threshold value for a luminance value. Here, the luminance value of the region of interest is, for example, a representative value, such as the average value of the pixel values of pixels included in the region of interest or the mode of the pixel values obtained from the pixel values of the pixels included in the region of interest. In a case where the luminance value of the region of interest is small while the region of interest displayed on the medical image is observed, it is difficult for a user to recognize the region of interest. Accordingly, in a case where the luminance value of the region of interest is equal to or smaller than the threshold value for a luminance value (in a case where the first condition is satisfied), the display control unit 66 makes a bounding box (similar to the bounding box 74 of FIG. 6 or the like), which surrounds the region of interest, be displayed in the first display region A1 as the notification information. Therefore, even in a case where the region of interest is dark, a user can recognize the region of interest and reliably make a diagnosis.

On the other hand, in a case where the luminance value of the region of interest is high, a user can recognize the region of interest even though there is no information notifying the user of the position of the region of interest, such as a bounding box. In this case, the display control unit 66 makes the bounding box, which is being displayed in the first display region A1, not be displayed in a case where the luminance value of the region of interest exceeds the threshold value for a luminance value (in a case where the second condition is satisfied). Further, the display control unit 66 makes an icon (similar to the icon 76 of FIG. 6 or the like), which represents that the region of interest is being detected, be displayed in the second display region A2 as the notification information. Accordingly, even though the bounding box 74 is made not to be displayed in the first display region A1, it is possible to prevent the region of interest from being missed.

Furthermore, in a case where the notification information is made to be displayed in the first display region A1 with the detection of the region of interest, the first condition may be a case where a first display time in which the notification information is displayed in the first display region A1 is equal to or shorter than a previously set display limit time and the second condition may be a case where the first display time exceeds the display limit time. Here, the first display time is counted with the start of the display of the notification information in the first display region A1.

In a case where the first display time is within the display limit time (in a case where the first condition is satisfied), the display control unit 66 makes a bounding box (similar to the bounding box 74 of FIG. 6 or the like), which surrounds the region of interest, be displayed in the first display region A1 as the notification information. Further, in a case where the first display time exceeds the display limit time (in a case where the second condition is satisfied), the display control unit 66 makes the bounding box not be displayed in the first display region A1. Furthermore, the display control unit 66 makes an icon (similar to the icon 76 of FIG. 6 or the like), which represents that the region of interest is being detected, be displayed in the second display region A2 as the notification information. Accordingly, a user can recognize the region of interest in a case where the bounding box is displayed for a fixed time. Therefore, the bounding box is made not to be displayed after a lapse of the fixed time, so that the observation of the medical image is not obstructed. Moreover, since the icon is displayed in the second display region A2 even though the bounding box 74 is made not to be displayed in the first display region A1, it is possible to prevent the region of interest from being missed.

Further, the first condition may be a case where a region where the notification information is to be displayed is designated as the first display region A1 by a user's input, and the second condition may be a case where the region where the notification information is to be displayed is designated as the second display region A2 by a user's input. A user's input may be made by a display region-designation part (not shown), which is provided on the operation part 12b of the endoscope 12, other than the console 19. In a case where the region is designated as the first display region A1 (in a case where the first condition is satisfied), the display control unit 66 makes the notification information be displayed in the first display region A1 in a condition where the region of interest is being detected. In a case where the region is designated as the second display region A2 (in a case where the second condition is satisfied), the display control unit 66 makes the notification information be displayed in the second display region A2 in a condition where the region of interest is being detected. In this case, the notification information may be made not to be displayed in the first display region A1 in a case where the notification information is being displayed in the first display region A1 before the region is designated as the second display region A2.

The first condition may be a case where combination information in which at least two of the area of the region of interest, the position of the region of interest, the temporal variation of the region of interest, the luminance value of the region of interest, and the first display time are combined satisfies a condition for combination; and the second condition may be a case where the combination information does not satisfy the condition for combination. For example, the first condition may be a case where area-luminance combination information in which the area of the region of interest and the luminance value of the region of interest are combined satisfies a combination condition for area-luminance, and the second condition may be a case where the area-luminance combination information in which the area of the region of interest and the luminance value of the region of interest are combined does not satisfy the combination condition for area-luminance.

Here, a case where the area-luminance combination information satisfies the combination condition for area-luminance (in a case where the first condition is satisfied) may include a case where the area of the region of interest is equal to or smaller than the threshold value for an area and the luminance value of the region of interest is equal to or smaller than the threshold value for a luminance value. In this case, the display control unit 66 makes a bounding box (similar to the bounding box 74 of FIG. 6 or the like), which surrounds the region of interest, be displayed in the first display region A1 as the notification information.

On the other hand, a case where the area-luminance combination information does not satisfy the combination condition for area-luminance (in a case where the second condition is satisfied) may include a case where the area of the region of interest exceeds the threshold value for an area and the luminance value of the region of interest is equal to or smaller than the threshold value for a luminance value, and a case where the area of the region of interest is equal to or smaller than the threshold value for an area and the luminance value of the region of interest exceeds the threshold value for a luminance value, and a case where the area of the region of interest exceeds the threshold value for an area and the luminance value of the region of interest exceeds the threshold value for a luminance value. In this case, the display control unit 66 makes the bounding box not be displayed in the first display region A1. Further, the display control unit 66 makes an icon (similar to the icon 76 of FIG. 6 or the like), which represents that the region of interest is being detected, be displayed in the second display region A2 as the notification information.

In a case where the display control unit 66 is to control the display of the notification information using the first and second conditions, the display control unit 66 may control the display of the notification information using a third condition different from the first condition and the second condition. In a case where the third condition is satisfied, the display control unit 66 performs control to make the notification information, which is being displayed in the second display region A2, not be displayed. Since the notification information is made not to be displayed in both the first display region A1 and the second display region A2 in a state where a user can reliably recognize the region of interest, it is possible to prevent the notification information from obstructing the observation of the medical image. The third condition includes, for example, a case where a second display time in which the notification information is displayed in the second display region A2 exceeds the display limit time. Here, the second display time is counted with the start of the display of the notification information in the second display region A2.

Further, in a case where a specific condition is satisfied, the display control unit 66 may perform control to make the notification information be displayed or control to make the notification information not be displayed in any one of the first display region A1, the second display region A2, or both the first display region A1 and the second display region A2. Furthermore, in a case where the specific condition is not satisfied, the display control unit 66 may perform control to make the notification information be displayed or control to make the notification information not be displayed in a display region that is different from the display region used in the case where the specific condition is satisfied. A case where the specific condition is satisfied may include "a case where the first condition is satisfied", and a case where the specific condition is not satisfied may include "a case where the second condition is satisfied".

For example, in a case where the specific condition is satisfied, the display control unit 66 makes the notification information be displayed in the first display region A1 and makes the notification information not be displayed in the second display region A2 in a condition where the region of interest is being detected. Further, in a case where the specific condition is not satisfied, the display control unit 66 makes the notification information be displayed in the second display region A2 and makes the notification information not be displayed in the first display region A1 in a condition where the region of interest is being detected. In a case where the specific condition is not satisfied, the display control unit 66 may make the notification information be displayed in both the first display region A1 and the second display region A2 in a condition where the region of interest is being detected. As described above, a user's input may be made by the display region-designation part, which is provided on the operation part 12b of the endoscope 12, other than the console 19.

Next, the control of display of the notification information performed by the display control unit 66 will be described with reference to a flowchart shown in FIG. 9. The endoscope 12 irradiates a subject with illumination light and picks up the image of the subject. A medical image is obtained from the image pickup of the subject. The region-of-interest detection section 70 detects a region of interest from the medical image. In a case where the region of interest is detected, notification information, which is used for the notification of information about the region of interest, is generated by the notification information-generation section 72. For example, a bounding box, which surrounds the region of interest, is generated as the notification information. The medical image and the notification information are sent to the display control unit 66.

The display control unit 66 performs control to make the medical image be displayed in the first display region A1 of the monitor 18. Further, the display control unit 66 performs control to make the notification information be displayed on the monitor 18 and control to make the notification information, which is being displayed, not be displayed on the monitor 18. The display control unit 66 controls the display of the notification information so that the display of the notification information does not obstruct the observation of the region of interest. In a case where the first condition is satisfied, such as a case where the area of the region of interest is small, the display control unit 66 makes the notification information be superimposed and displayed on the medical image in the first display region A1. For example, the region of interest is displayed to be surrounded by the bounding box. Furthermore, the region of interest may be displayed in a state where the region of interest is painted with a specific color or a translucent color is superimposed on the region of interest. In this case, the color to be superimposed may be changed according to the contents of the notification information.

In contrast, in a case where the second condition is satisfied, such as a case where the area of the region of interest is large, the display control unit 66 makes the notification information be displayed in the second display region A2. In this case, the notification information displayed in the first display region A1 is made not to be displayed in a case where the notification information is being displayed in the first display region A1. For example, in a case where a bounding box is being displayed in the first display region A1, the bounding box is made not to be displayed in the first display region A1 and an icon representing that the region of interest is being detected is made to be displayed in the second display region A2. Accordingly, even though the bounding box is made not to be displayed, it is possible to prevent the region of interest from being missed. The control of display of the notification information performed by the above-mentioned display control unit 66 is repeatedly performed until the observation of the region of interest ends. An instruction to end the observation of the region of interest is given by the operation of the console 19 or the like.

Second Embodiment

In a second embodiment, the error of a subject image or a medical image is displayed on the monitor 18 as notification information. Accordingly, as shown in FIG. 10, an image processing unit 61 of the second embodiment is provided with an image analysis section 80 for error detection, which detects an error from a medical image, as an error detection section, which detects an error, in addition to the region-of-interest detection section 70. A sensor for error detection may be used as the error detection section to detect an error. The sensor for error detection may be provided not only on the distal end part 12d of the endoscope 12 but also on a treatment tool to be inserted into a forceps channel. Further, since a region of interest does not need to be detected as long as an error can be detected, the image processing unit 61 may not be provided with the region-of-interest detection section 70 in the second embodiment.

The image analysis section 80 for error detection detects a blur, which appears on a medical image, as an error. This blur occurs due to the movement of at least one of a subject or the distal end part of the endoscope 12. As a method of detecting a blur, there is, for example, a method including calculating a high-frequency component of a medical image and determining that a blur occurs in a case where the high-frequency component is equal to or smaller than a fixed value. Further, the image analysis section 80 for error detection detects the degree of contamination of the subject as an error. Examples of the contamination of the subject include residue, residual liquid, and the like. As a method of detecting the degree of contamination of the subject, there is, for example, a method including calculating color information (for example, a ratio of B images to G images and a ratio of G images to R images) from a medical image, and calculating the degree of contamination of the subject by comparing the calculated color information with contamination-color information corresponding to contamination on the subject. In this case, the degree of contamination of the subject is higher as the calculated color information is closer to the contamination-color information.

Furthermore, a notification information-generation section 72 of the second embodiment generates notification information that is used for the notification of an error. Examples of the notification information include character information that represents the generation of an error and the type of the error. In a case where an error is a blur appearing on the medical image, it is preferable that the notification information is character information of "blur occurrence" representing the generation of a blur. Further, in a case where an error is the contamination of a subject, it is preferable that the notification information is character information of "contamination occurrence (medium degree)" representing the occurrence of contamination and the degree of contamination.

The display control unit 66 controls the display of the notification information so that the display of the notification information does not obstruct the observation of the medical image. Specifically, in a case where a specific condition to be used for the detection of an error is satisfied, the display control unit 66 makes the notification information (the character information of "blur occurrence" in FIG. 11) be displayed in the second display region A2 as shown in FIG. 11. Here, it is preferable that the specific condition is a condition, which is related to the detection of an error, of the first and second conditions described in the first embodiment.

In a case where the specific condition is not satisfied due to a change in the state thereafter, the display control unit 66 makes the notification information not be displayed in the second display region A2. In a case where the detection of an error continues for a predetermined time or longer even though the specific condition is not satisfied, the display control unit 66 may continue to make the notification information be displayed in the second display region A2. Further, the notification information may be made to be displayed in the first display region A1 instead of or in addition to the second display region A2.

Third Embodiment

In a third embodiment, the observation state of a subject is displayed on the monitor 18 as notification information. There are various observation states of a subject using the endoscope system 10. For example, in the endoscope system 10, a subject can be irradiated with a plurality of kinds of illumination light having different wavelengths or the like. Accordingly, the observation state of the subject can be changed according to a plurality of illumination modes where different types of illumination light are used.

In the endoscope system 10, a plurality of kinds of image processing can be performed on a medical image that is obtained from the image pickup of the subject. Accordingly, the observation state of the subject can be changed according to a plurality of image processing modes where different types of image processing are performed on the medical image. Further, the endoscope system 10 can increase the size of the subject by the operation of the zoom operation part 13. Accordingly, the observation state of the subject can be changed according to non-enlargement observation where the image of the subject is not enlarged or enlargement observation where the image of the subject is enlarged.

As shown in FIG. 12, an image processing unit 61 of the third embodiment is provided with an observation state-acquisition section 81, which acquires the observation state of a subject in addition to the region-of-interest detection section 70. The observation state-acquisition section 81 can communicate with not only the processor device 16 but also the endoscope 12 or the light source device 14. Accordingly, the observation state-acquisition section 81 acquires an illumination mode or an image processing mode, which is currently in use in the image processing unit 61, as the observation state of the subject. Further, the observation state-acquisition section 81 acquires non-enlargement observation or enlargement observation as the observation state of the subject according to the state of the operation performed by the zoom operation part 13.

Furthermore, a notification information-generation section 72 of the third embodiment generates notification information that is used for the notification of the observation state of the subject. Examples of the notification information include character information that represents the observation state of the subject. In a case where the observation state of the subject is represented as the illumination mode, it is preferable that the notification information is character information about the illumination mode currently in use (for example, "white light mode" in a case where white light is used as illumination light). Further, in a case where the observation state of the subject is represented as the image processing mode, it is preferable that the notification information is character information about the image processing mode currently in use (for example, "white image mode" in a case where a white image obtained from the image pickup of the subject illuminated with white light is subjected to image processing). Furthermore, it is preferable that the notification information is character information about the "non-enlargement observation" in a case where the observation state of the subject is the non-enlargement observation and the notification information is character information about the "enlargement observation" in a case where the observation state of the subject is the enlargement observation.

The display control unit 66 controls the display of the notification information so that the display of the notification information does not obstruct the observation of the medical image. Specifically, in a case where a specific condition is satisfied, the display control unit 66 makes the notification information (the character information of "white light mode" in FIG. 13) be displayed in the second display region A2 as shown in FIG. 13. Here, it is preferable that the specific condition is a condition, which is related to the observation state of the subject, of the first and second conditions described in the first embodiment.

In a case where the specific condition is not satisfied due to a change in the state thereafter, the display control unit 66 makes the notification information not be displayed in the second display region A2. In a case where separate designation is made through the operation of the console 19 or the like by a user even though the specific condition is not satisfied, the display control unit 66 may continue to make the notification information be displayed in the second display region A2. Further, the notification information may be made to be displayed in the first display region A1 instead of or in addition to the second display region A2. Furthermore, in a case where the observation state of the subject is changed, the display control unit 66 may make the type of the notification information be switched. For example, in a case where a mode is changed from a white light mode into a special light mode where light in a specific wavelength range is used, the display control unit 66 switches the notification information into the "special light mode" from the "white light mode". Further, the notification information may be made not to be displayed after continuing to be displayed for a fixed time.

Fourth Embodiment

In a fourth embodiment, whether or not a lesion is present, the type of a lesion, or the detection state of a treatment tool is displayed on the monitor 18 as notification information. As shown in FIG. 14, a discrimination processing section 82 discriminates whether or not a lesion is present and the type of a lesion on the basis of a feature quantity that is included in a region of interest. The discrimination processing section 82 calculates whether or not a lesion is present in a region of interest and the type of a lesion by using discrimination processing, such as a convolutional neural network. Further, a treatment tool-detection section 84 detects a treatment tool on the basis of a feature quantity that is included in the region of interest. The treatment tool-detection section 84 detects whether or not the treatment tool is included in the region of interest by using treatment tool-detection processing, such as a convolutional neural network.

Furthermore, a notification information-generation section 72 of the fourth embodiment generates notification information that is used for the notification of the observation state of the subject. In a case where the notification information is whether or not a lesion is present or the type of a lesion, it is preferable that the notification information-generation section 72 generates a discrimination score value 88 representing the degree of progression of a lesion or lesioness and a seek bar 90 moving according to the discrimination score value 88 as the notification information as shown in FIG. 15. As the score value is higher, the discrimination score value 88 represents that the possibility of a lesion is higher. As the discrimination score value 88 is higher, the length Ls of the seek bar 90 is larger. Further, in a case where the notification information is whether or not a treatment tool is present, it is preferable that the notification information-generation section 72 generates character information (for example, "detection of presence of treatment tool" or the like) representing whether or not a treatment tool is present as the notification information.

The display control unit 66 controls the display of the notification information so that the display of the notification information does not obstruct the observation of a medical image. Specifically, in a case where a specific condition is satisfied, the display control unit 66 makes the notification information (the discrimination score value 88 and the seek bar 90 in FIG. 16) be displayed in the second display region A2 as shown in FIG. 16. In a case where the specific condition is not satisfied due to a change in the state thereafter, the display control unit 66 makes the notification information not be displayed in the second display region A2. In a case where separate designation is made through the operation of the console 19 or the like by a user even though the specific condition is not satisfied, the display control unit 66 may continue to make the notification information be displayed in the second display region A2. Further, the notification information may be made to be displayed in the first display region A1 instead of or in addition to the second display region A2.

The display control unit 66 may perform control to make a combination of two or more among "the information about the region of interest" described in the first embodiment, "the error of a subject or a medical image" described in the second embodiment, "the observation state of a subject" described in the third embodiment, and "whether or not a lesion is present, the type of a lesion, and the detection state of a treatment tool" described in the fourth embodiment as the notification information, which is to be notified to a user, be displayed or not be displayed in the first display region A1 or the second display region.

The invention has been applied to the endoscope system 10 in the first to fourth embodiments. However, the invention is not limited to the endoscope system 10, and can be applied to a medical image processing device for processing a medical image. Further, the invention can also be applied to a diagnosis support device that supports diagnosis for a user by using a medical image. Furthermore, the invention can also be applied to a medical service support device that supports a medical service, such as a diagnosis report, by using a medical image.

It is preferable that the medical image used in the first to fourth embodiments is a normal light image obtained from the application of light in a white-light wavelength range or light in a plurality of wavelength ranges as the light in the white-light wavelength range.

Further, it is preferable that the medical image used in the first to fourth embodiments is a special light image obtained from the application of light in a specific wavelength range. It is preferable that the light in the specific wavelength range is in a wavelength range narrower than the white-light wavelength range. It is preferable that the specific wavelength range is included in a blue-light wavelength range or a green-light wavelength range of a visible-light wavelength range. It is preferable that the specific wavelength range has a peak in the wavelength range of 390 nm to 450 nm or 530 nm to 550 nm.

It is preferable that the specific wavelength range is included in a red-light wavelength range of the visible-light wavelength range. It is preferable that the specific wavelength range has a peak in the range of 585 nm to 615 nm or 610 nm to 730 nm.

It is preferable that the specific wavelength range has a peak in a wavelength range where an absorption coefficient in oxyhemoglobin is different from that in reduced hemoglobin. It is preferable that the specific wavelength range has a peak in the wavelength range of 400±10 nm, 440±10 nm, 470±10 nm, or 600 nm to 750 nm.

Further, it is preferable that the medical image used in the first to fourth embodiments is an in-vivo image of the inside of a living body. It is preferable that the in-vivo image includes information about the fluorescence of a fluorescent material present in the living body. It is preferable that the fluorescence is obtained from the irradiation of the inside of the living body with excitation light having a peak in the wavelength range of 390 to 470 nm.

Furthermore, it is preferable that the medical image used in the first to fourth embodiments is an in-vivo image of the inside of a living body. It is preferable that the specific wavelength range is an infrared wavelength range. It is preferable that the specific wavelength range has a peak in the wavelength range of 790 nm to 820 nm or 905 nm to 970 nm.

Further, it is preferable that the image acquisition unit 54 acquiring the medical image used in the first to fourth embodiments includes a special-light-image acquisition section acquiring a special light image, which includes a signal in the specific wavelength range, on the basis of the normal light image obtained from the application of light in the white-light wavelength range or light in a plurality of wavelength ranges as the light in the white-light wavelength range. It is preferable that the medical image is the special light image. It is preferable that the signal in the specific wavelength range is obtained from an arithmetic operation based on color information about RGB or CMY included in the normal light image.

Furthermore, it is preferable that the medical image used in the first to fourth embodiments is a feature quantity image. It is preferable that a feature-quantity-image generation section generating the feature quantity image generates the feature quantity image from an arithmetic operation based on at least one of the normal light image, which is obtained from the application of light in the white-light wavelength range or light in a plurality of wavelength ranges as the light in the white-light wavelength range, and the special light image, which is obtained from the application of light in the specific wavelength range.

EXPLANATION OF REFERENCES

10: endoscope system (medical image processing device)
12: endoscope
12*a*: insertion part
12*b*: operation part
12*c*: bendable part
12*d*: distal end part
12*e*: angle knob
12*f*: forceps inlet
13: zoom operation part
14: light source device
16: processor device
18: monitor
19: console
20: light source unit
22: light source control unit
30*a*: illumination optical system
30*b*: image pickup optical system
41: light guide
45: illumination lens
46: objective lens
47: zoom lens
48: image sensor
52: control unit
54: image acquisition unit
56: DSP (Digital Signal Processor)
58: noise-reduction section
59: conversion section
61: image processing unit
66: display control unit
68: recording control unit
69: storage memory
70: region-of-interest detection section
72: notification information-generation section 74: bounding box
76: icon
80: image analysis section for error detection
81: observation state-acquisition section
82: discrimination processing section
84: treatment tool-detection section
88: discrimination score value
90: seek bar

What is claimed is:

1. A medical image processing device comprising a processor and a display,
wherein the display is configured to:
display the medical image in a first display region; and
the processor is configured to:
acquire a medical image including a subject;
perform control to make notification information, which is to be notified to a user, be displayed on the display or control to make the notification information not be displayed on the display; and
detect a region of interest from the medical image,
wherein the processor
performs control to make the notification information be displayed in a second display region different from the first display region or control to make the notification information, which is being displayed, not be displayed in the second display region,
performs control to make the notification information be displayed in the first display region in a case where a first condition is satisfied, and
performs control to make the notification information, which is being displayed in the first display region, not be displayed and to make the notification information be displayed in the second display region in a case where a second condition different from the first condition is satisfied,
wherein the first condition is a case where an area of the region of interest is equal to or smaller than a threshold value for an area, and the second condition is a case where the area of the region of interest exceeds the threshold value for an area.

2. The medical image processing device according to claim 1,
wherein the processor performs control to superimpose and display the notification information on the medical image in the first display region.

3. The medical image processing device according to claim 2, the processor further configured to:
generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
wherein the medical image is the feature quantity image.

4. The medical image processing device according to claim 1, the processor further configured to:
generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
wherein the medical image is the feature quantity image.

5. A medical image processing device comprising a processor and a display, wherein the display is configured to:
display the medical image in a first display region; and
the processor is configured to:
acquire a medical image including a subject;
perform control to make notification information, which is to be notified to a user, be displayed on the display or control to make the notification information not be displayed on the display; and
detect a region of interest from the medical image,
wherein the processor
performs control to make the notification information be displayed in a second display region different from the first display region or control to make the notification information, which is being displayed, not be displayed in the second display region,
performs control to make the notification information be displayed in the first display region in a case where a first condition is satisfied, and
performs control to make the notification information, which is being displayed in the first display region, not be displayed and to make the notification information be displayed in the second display region in a case where a second condition different from the first condition is satisfied,
wherein the first condition is a case where a position of the region of interest is away from a central range of the first display region, and
the second condition is a case where the position of the region of interest is in the central range of the first display region.

6. The medical image processing device according to claim 5,
wherein the processor performs control to superimpose and display the notification information on the medical image in the first display region.

7. The medical image processing device according to claim 6, the processor further configured to:
generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
wherein the medical image is the feature quantity image.

8. The medical image processing device according to claim 5, the processor further configured to:
generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
wherein the medical image is the feature quantity image.

9. A medical image processing device comprising a processor and a display,
wherein the display is configured to:
display the medical image in a first display region; and
the processor is configured to:
acquire a medical image including a subject;
perform control to make notification information, which is to be notified to a user, be displayed on the display or control to make the notification information not be displayed on the display; and detect a region of interest from the medical image,
wherein the processor
  performs control to make the notification information be displayed in a second display region different from the first display region or control to make the notification information, which is being displayed, not be displayed in the second display region,
  performs control to make the notification information be displayed in the first display region in a case where a first condition is satisfied, and
  performs control to make the notification information, which is being displayed in the first display region, not be displayed and to make the notification information be displayed in the second display region in a case where a second condition different from the first condition is satisfied,
wherein the first condition is a case where a temporal variation of the region of interest exceeds a threshold value for variation, and
the second condition is a case where the temporal variation of the region of interest is equal to or smaller than the threshold value for variation.

10. The medical image processing device according to claim 9,
  wherein the processor performs control to superimpose and display the notification information on the medical image in the first display region.

11. The medical image processing device according to claim 10, the processor further configured to:
  generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
  wherein the medical image is the feature quantity image.

12. The medical image processing device according to claim 9, the processor further configured to:
  generate a feature quantity image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range,
  wherein the medical image is the feature quantity image.

* * * * *